US012617129B2

(12) United States Patent
Tanriverdi

(10) Patent No.: US 12,617,129 B2
(45) Date of Patent: May 5, 2026

(54) METHOD OF MANUFACTURING A MICROFLUIDIC ARCHITECTURE

(71) Applicant: Unhindr LTD, London (GB)

(72) Inventor: Ugur Tanriverdi, London (GB)

(73) Assignee: Unhindr LTD, London (GB)

( * ) Notice: Subject to any disclaimer, the term of this patent is extended or adjusted under 35 U.S.C. 154(b) by 1035 days.

(21) Appl. No.: 17/761,925

(22) PCT Filed: Sep. 18, 2020

(86) PCT No.: PCT/GB2020/052267
§ 371 (c)(1),
(2) Date: Mar. 18, 2022

(87) PCT Pub. No.: WO2021/053350
PCT Pub. Date: Mar. 25, 2021

(65) Prior Publication Data
US 2022/0371232 A1      Nov. 24, 2022

(30) Foreign Application Priority Data
Sep. 19, 2019    (GB) ...................................... 1913529

(51) Int. Cl.
*B29C 39/12*         (2006.01)
*A61F 2/50*          (2006.01)
(Continued)

(52) U.S. Cl.
CPC .......... *B29C 39/123* (2013.01); *A61F 2/7812* (2013.01); *B29C 39/26* (2013.01);
(Continued)

(58) Field of Classification Search
CPC ..... B29C 39/021; B29C 39/025; B29C 39/10; B29C 39/12
See application file for complete search history.

(56) References Cited

U.S. PATENT DOCUMENTS 3,832,264 A *   8/1974   Barnette ................... B44F 9/04
                                                52/630
5,871,830 A *   2/1999   Miller .................... D21H 13/24
                                                428/68

(Continued)

FOREIGN PATENT DOCUMENTS

CN         101072635 A     11/2007
CN         101149364 A     3/2008
(Continued)

*Primary Examiner* — Jeffrey M Wollschlager
(74) *Attorney, Agent, or Firm* — Hall Estill Law Firm

(57)                ABSTRACT

A method of manufacturing a microfluidic architecture having at least one channel disposed therein. Steps can include pouring an uncured polymeric material into a mould to produce a first layer; at least partially curing the first layer; and forming the at least one channel by disposing a support material on the first layer; pouring an uncured polymeric material onto the first layer to form a second layer to thereby encapsulate the support material; and at least partially curing the second layer such that the first layer and second layer together form the microfluidic architecture; wherein the support material undergoes a phase change during the process of forming the at least one channel. The phase change of the support material enables the material to be more easily disposed and/or removed after formation of the channel.

28 Claims, 8 Drawing Sheets

(51) Int. Cl.
  *A61F 2/78* (2006.01)
  *B29C 39/26* (2006.01)
  *B29L 31/00* (2006.01)
  *B81B 1/00* (2006.01)
  *B81C 99/00* (2010.01)

(52) U.S. Cl.
  CPC .......... *B81B 1/002* (2013.01); *B81C 99/0085* (2013.01); *A61F 2002/5012* (2013.01); *A61F 2002/5053* (2013.01); *B29L 2031/756* (2013.01); *B81B 2201/058* (2013.01); *B81B 2203/0338* (2013.01)

(56) References Cited

U.S. PATENT DOCUMENTS

| | | | | |
|---|---|---|---|---|
| 7,125,510 | B2* | 10/2006 | Huang | B29C 39/10 |
| | | | | 264/225 |
| 7,494,557 | B1* | 2/2009 | Peterson | H05K 1/0272 |
| | | | | 264/43 |
| 7,686,907 | B1 | 3/2010 | Woolley et al. | |
| 9,458,357 | B2 | 10/2016 | Bellan et al. | |
| 9,574,172 | B2 | 2/2017 | Lenardi et al. | |
| 2002/0100714 | A1* | 8/2002 | Staats | H01J 49/04 |
| | | | | 204/600 |
| 2002/0134907 | A1* | 9/2002 | Benett | B29C 39/34 |
| | | | | 264/219 |
| 2002/0164816 | A1 | 11/2002 | Quake | |
| 2003/0156992 | A1 | 8/2003 | Anderson et al. | |
| 2003/0214057 | A1 | 11/2003 | Huang | |
| 2004/0086424 | A1* | 5/2004 | Schembri | B01L 3/505 |
| | | | | 422/504 |
| 2005/0069462 | A1 | 3/2005 | Humenik et al. | |
| 2007/0012891 | A1 | 1/2007 | Maltezos et al. | |
| 2007/0028969 | A1 | 2/2007 | Bovd et al. | |
| 2007/0183933 | A1 | 8/2007 | Hiroshi et al. | |
| 2008/0305343 | A1 | 12/2008 | Toohey et al. | |
| 2009/0281250 | A1* | 11/2009 | DeSimone | C08G 65/007 |
| | | | | 427/508 |
| 2011/0315310 | A1* | 12/2011 | Trevisan | B29C 70/46 |
| | | | | 156/245 |
| 2012/0128549 | A1 | 5/2012 | Zhou et al. | |
| 2013/0189888 | A1 | 7/2013 | Patrick et al. | |
| 2014/0004501 | A1* | 1/2014 | Talebpour | C12N 1/066 |
| | | | | 435/173.6 |
| 2015/0137429 | A1 | 5/2015 | Chung | |
| 2015/0352549 | A1* | 12/2015 | Kolb | B29C 65/16 |
| | | | | 422/539 |
| 2016/0096176 | A1 | 4/2016 | Jarvius et al. | |
| 2016/0144362 | A1* | 5/2016 | Lee | B01D 19/0031 |
| | | | | 436/175 |
| 2016/0175840 | A1 | 6/2016 | Ingber et al. | |
| 2018/0117588 | A1 | 5/2018 | Ingber et al. | |
| 2018/0126375 | A1* | 5/2018 | Saggiomo | B29C 33/52 |
| 2018/0279702 | A1 | 10/2018 | Karbakhsh | |
| 2019/0184393 | A1 | 6/2019 | Mahmud et al. | |
| 2019/0299169 | A1* | 10/2019 | Torniainen | B01F 25/31 |

FOREIGN PATENT DOCUMENTS

| | | | |
|---|---|---|---|
| CN | 1988764 | B | 7/2012 |
| CN | 103009534 | A | 4/2013 |
| CN | 106215986 | * | 12/2016 |
| CN | 106215986 | A | 12/2016 |
| CN | 107208731 | A | 9/2017 |
| CN | 107283859 | A | 10/2017 |
| CN | 111836722 | A | 10/2020 |
| DE | 19850046 | A1 | 5/2000 |
| EP | 0282840 | A2 | 9/1988 |
| EP | 2213615 | A2 | 8/2010 |
| EP | 2444157 | A1 | 4/2012 |
| EP | 2826814 | A1 | 1/2015 |
| EP | 3201690 | | 9/2017 |
| EP | 3177444 | B1 | 12/2019 |
| EP | 3201690 | B1 | 12/2019 |
| GB | 2572165 | A | 9/2019 |
| WO | 2001001025 | A2 | 1/2001 |
| WO | 2001001025 | A3 | 1/2001 |
| WO | 2002043615 | | 6/2002 |
| WO | 2002043615 | A2 | 6/2002 |
| WO | 2002043615 | A3 | 6/2002 |
| WO | 2005084191 | | 9/2005 |
| WO | 2005084191 | A2 | 9/2005 |
| WO | 2005084191 | A3 | 9/2005 |
| WO | WO2005084792 | A1 | 9/2005 |
| WO | 2007021762 | | 2/2007 |
| WO | 2007021762 | A2 | 2/2007 |
| WO | 2007021762 | A3 | 2/2007 |
| WO | 2007061448 | A2 | 5/2007 |
| WO | 2007061448 | A3 | 5/2007 |
| WO | 2007092472 | | 8/2007 |
| WO | 2007092472 | A1 | 8/2007 |
| WO | 2013019491 | A1 | 7/2013 |
| WO | 2016155760 | | 10/2016 |
| WO | 2016155760 | A1 | 10/2016 |
| WO | 2016198880 | A1 | 12/2016 |
| WO | 2019166279 | A1 | 9/2019 |
| WO | 2019180431 | A1 | 9/2019 |
| WO | 2021053350 | | 3/2021 |

* cited by examiner

METHOD OF MANUFACTURING A MICROFLUIDIC ARCHITECTURE

Related Applications

The present application makes a claim of priority to PCT/GB2020/052267 filed Sep. 18, 2020, which in turn makes a claim of priority to GB 1913529.2 filed Sep. 19, 2019, the contents of these applications being incorporated by reference.

BACKGROUND TO THE INVENTION

The present invention relates to microfluidic architectures, such as microfluidic chips, and a method of manufacturing such architectures. Such architectures include small channels through which fluid can pass, and may be made from polymeric materials. Production of such microfluidic architectures requires high precision manufacturing, and the size of channels which can be incorporated into such architectures may be limited by the manufacturing processes and/or materials available.

When polymeric materials are used to produce microfluidic architectures, a support structure is typically used to maintain the shape of the channels within the polymeric architecture during curing of the polymeric material. However, it may then be difficult to remove the material which is used to support the channels after the curing has been completed.

In some known methods, soluble materials such as sugar may be used as a material to support the channels during curing. Other soluble materials may also be used, such as a soluble material which can be deposited using additive layer manufacturing. In this approach, water or another liquid may be used to dissolve the soluble material in order to remove the support substance after curing. However, if the channels have complex shapes, or are long, it may be difficult to remove the soluble material due to the length and complexity of the channel.

It is an aim of the present invention to at least partially address the problems noted above.

SUMMARY OF THE INVENTION

According to the present disclosure, there is provided a method of manufacturing a microfluidic architecture comprising at least one channel disposed therein, the method comprising pouring an uncured polymeric material into a mould to produce a first layer, at least partially curing the first layer, and forming the at least one channel by, disposing a support material on the first layer, pouring an uncured polymeric material onto the first layer to form a second layer to thereby encapsulate the support material, and at least partially curing the second layer such that the first layer and second layer together form the microfluidic architecture, wherein the support material undergoes a phase change during the process of forming the at least one channel. That is, the phase of the support material itself may change from a solid, a liquid, or a gas, to another of a solid, a liquid or a gas. This may allow the support material to be more easily disposed and/or removed than arrangements in which a solid material is dissolved by a different liquid.

Optionally, the first layer comprises at least one open channel, the support material is a fluid when disposed on the first layer, and forming the at least one channel includes: at least partially filling the open channel with the fluid, solidifying the fluid, thereby providing said phase change, closing at least a portion of the channel by pouring the uncured polymeric material onto the first layer to form the second layer to thereby encapsulate the solidified support material. That is, disposing the support material on the first layer includes at least partially filling the open channel with the fluid. The phase change is solidifying the support material. This may allow the shape of the channels to be determined by the mould, and the support material to be easily disposed on the first layer.

Optionally, the fluid is a liquid, and the phase change is solidifying the liquid by freezing.

Optionally, the support material is a solid when disposed on the first layer. This may allow the shape of the channels to be pre-formed as a separate component.

Optionally, wherein the phase change is a sublimation. This may allow the support material to be more easily removed than arrangements in which the material is dissolved in a liquid.

Optionally, the polymeric material is an elastomeric material. Optionally, the elastomeric material comprises one or more of a silicone, acrylic, a nitrile, a rubber, and polyurethane.

Optionally, the method further comprises removing the support material from the channel.

Optionally, the steps of removing the support material from the channel and curing the second layer temporally overlap.

Optionally, the method further comprises pouring an uncured polymeric material into a mould to produce a third layer, at least partially curing the third layer, disposing the third layer on the second layer before curing of the second layer is complete, and curing the second and third layers together such that bonds are formed between the second and third layer. This may allow multiple layered architectures to be formed.

Optionally, the method further comprises filling an open channel in the third layer with a fluid, solidifying said liquid, closing at least a portion of the channel by pouring an uncured polymeric material onto the third layer to form a fourth layer to thereby encapsulate the solidified fluid, and at least partially curing the fourth layer such that the third layer and fourth layer are joined to the microfluidic architecture. This may allow multiple layers of channels to be formed in a single architecture.

Optionally, the curing of the second layer of polymeric material causes bonds to be formed between at least two of the layers.

Optionally, the channel comprises at least one opening through at least one of the layers. Optionally, the channel comprises a plurality of openings through at least one of the layers. This may allow fluid to be introduced into and removed from the architecture.

Optionally, the channel comprises openings at opposite ends of the microfluidic architecture.

Optionally, the method further comprises disposing an electronic component through at least one opening. This may allow the architecture to be used as a flow control component.

Optionally, the open channel is a partial ellipse in cross-section.

Optionally, the at least one channel is a network of channels.

Optionally, the network of channels includes a manifold arranged to receive and/or store a fluid and a plurality of branches in fluid connection with the manifold.

Optionally, the support material is water.

Optionally, the step of freezing takes place at –30 degrees Celsius or less, preferably –50 degrees Celsius or less, and more preferably –80 degrees Celsius or less.

Optionally, the method further comprises disposing an additional support material on the first layer, wherein the additional support material is different from the support material, the additional support material does not undergo a phase change during the process of forming the channel, and the support material is retained between the first and second layers.

Optionally, the additional support material is a substantially flat sheet, preferably waxed paper or a metal foil.

Optionally, the additional support material is arranged to interact with a fluid disposed in the microfluidic architecture.

According to the present disclosure, there is also provided a method of manufacturing a microfluidic architecture comprising at least one channel disposed therein, the method comprising pouring an uncured polymeric material into a mould to produce a first layer, at least partially curing the first layer, forming the at least one channel by disposing a support material on the first layer pouring an uncured polymeric material onto the first layer to form a second layer to thereby encapsulate the support material, and at least partially curing the second layer such that the first layer and second layer together form the microfluidic architecture, wherein the support material does not undergo a phase change during the process of forming the at least one channel, and the support material is retained between the first and second layers.

Optionally, the support material is arranged to interact with a fluid disposed in the microfluidic architecture.

According to the present disclosure, there is also provided a microfluidic architecture obtainable by the methods set out above.

According to the present disclosure, there is also provided a microfluidic architecture comprising a network of channels, wherein the network of channels includes a manifold arranged to receive and/or store fluid and a plurality of branches in fluid connection with the manifold, wherein the microfluidic architecture is a flexible sheet.

Optionally, the microfluidic architecture is a microfluidic chip.

Optionally, the architecture comprises two channels joined in selective fluid communication by an electronic component.

Optionally, at least one channel is arranged to receive a fluid to cause an increase in at least one of the surface area or the volume of the microfluidic architecture and/or at least one channel is arranged to change in volume to thereby allow or prevent flow through another channel in the architecture.

According to the present disclosure, there is also provided a liner for a device arranged for skin contact comprising at least one microfluidic architecture as set out above.

BRIEF DESCRIPTION OF THE DRAWINGS

The present invention will now be described, by way of non-limitative example only, with reference to the accompanying drawings, in which.

DETAILED DESCRIPTION

The present invention provides a method of manufacturing a microfluidic architecture including at least one channel inside the microfluidic architecture. The architecture may be a microfluidic chip. Such a microfluidic chip may have one or more channels disposed in the inside of the chip, which allow fluids to pass through. In particular, the architecture may include a network of channels which can be used in many different applications. For example, the chip may be formed of a flexible material such as an elastomeric polymer, and in particular an elastomer. Such a chip may include a flexible manifold. That is, fluid may be retained inside the chip and moved around inside the chip and/or to other components connected to the chip.

The method of manufacturing the microfluidic architecture will now be described with reference to FIGS. 1-7, where a simplified representation including a single channel is shown. However, it will be understood that the channel may form a network of channels of any suitable shape, as shown, for example, in FIGS. 8 and 9.

Figure 1:
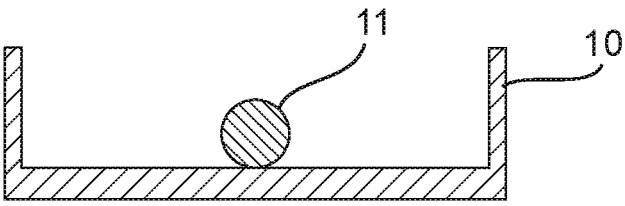
FIG. 1 shows a mould for use in manufacturing a microfluidic architecture.
Figure 11:
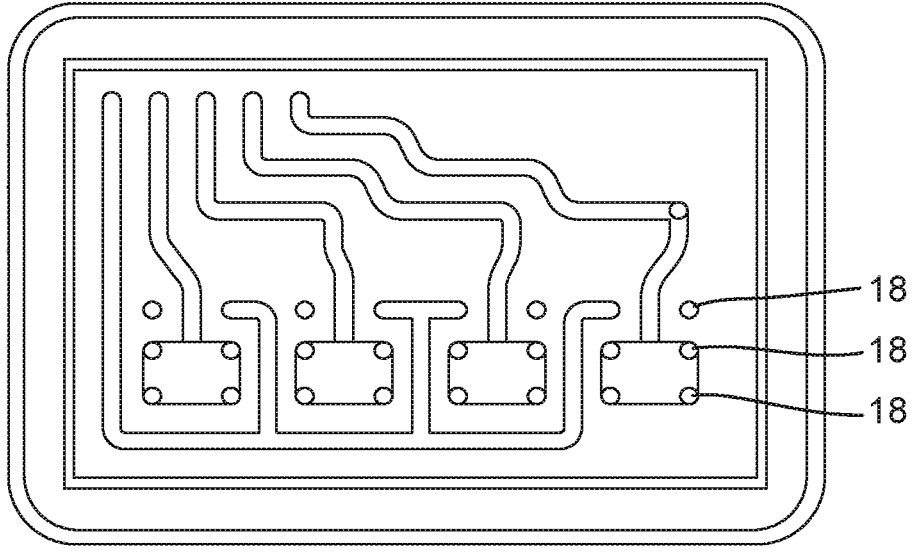
FIG. 11 shows a mould for use in a method of manufacturing the architecture of FIG. 10.

A mould 10 is used to produce a first layer of the architecture. As shown in FIG. 1, the mould may have a raised part 11 which corresponds to the desired shape and location of a channel in the architecture. Although a single raised part corresponding to a single channel is shown in FIG. 11, more complicated shapes of mould may be used to produce corresponding more complicated shapes of channel, such as those shown in FIG. 8, where a network of channels is provided, spanning from one side of the mould to the other.

Figure 2:
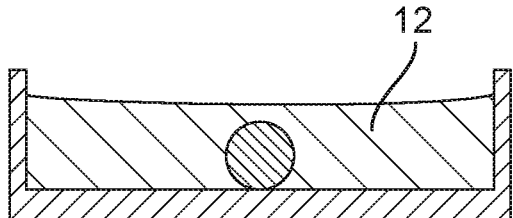
FIG. 2 shows a first layer of uncured polymeric material in a mould.

As shown in FIG. 2, an uncured polymeric material is poured into the mould 10 in order to form a first layer 12. The first layer is then at least partially cured so that it retains the shape defined by the mould 10. The curing process may be carried out using any suitable method known in the art, including chemically initiated curing or (for e.g. a thermosetting material) curing induced by heat or radiation. If the first layer is partially cured, the layer may maintain the shape defined by the mould once it is removed from the mould, but may still retain the capacity to form further bonds with (i.e. to join to) further layers of polymeric material, as will be described below.

Figure 3:
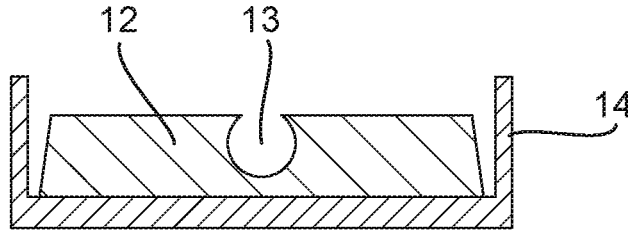
FIG. 3 shows a cured first layer including an open channel.

As shown in FIG. 3, which shows the first layer 12 after (partial) curing and being removed from the mould 10, an open channel 13 is formed at the location of the raised portion 11 of the mould. It will be noted that the first layer 12 has been turned over in FIG. 3 such that the open channel faces upward. At this stage, the first layer 12 may be placed in a second mould 14 for use in subsequent steps, or, as described below, this may be done later on in the method. As shown in FIG. 3, the open channel is open to one of the surfaces of the first layer 12, and appears in cross-section as an indentation in the surface of the first layer 12. In the arrangement shown in in FIG. 3, the top surface of the first layer 12 is narrower than the bottom surface of the first layer. This is because, when the uncured elastomer is poured, a meniscus may form, as shown in FIG. 2. This may result in the bottom surface of the first layer 12 in FIG. 3 (i.e. the top surface of the first layer 12 in FIG. 2) being longer than the top surface of the first layer 12 in FIG. 3, leading to the shape shown in FIG. 3. However, depending on the material used, a meniscus may not form, or it may be negligible, so the cross-section of the first layer 12 may also be a rectangle, as opposed to the trapezium shown in FIG. 3.

Typically, the cross-section of the open channel is part of an ellipse, such as a semicircle or an ellipse with part of its circumference removed, as shown in FIG. 3. Depending on the material used, different cross-sectional shapes of channel may be used. For generally flexible materials, a cross-sectional shape which is an ellipse with less than half of its circumference, as shown in FIG. 3, may be used. In such a case, the flexibility of the material may allow removal of the first layer 12 from the mould. For less flexible materials, a semi-ellipse or an elliptical shape with more than half of its circumference removed may be used, in order to ease removal of the first layer 12 from the mould 10. It will be understood that a circle is a particular example of an ellipse. It will also be understood that the cross-section may have any other geometry, in accordance with the desired shape of channel.

Figure 4:
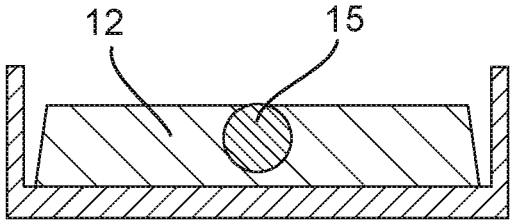
FIG. 4 shows the layer of FIG. 3 with the open channel filled with a liquid.

The open channel 13 is then at least partially filled with a liquid 15, as shown in FIG. 4. The liquid 15 acts as a support material. The liquid 15 may be water, or may be any other suitable liquid which can be frozen at an appropriate temperature. For example, additives which change the physical or chemical properties of the liquid may be added to the liquid. Such additives may, for example, react with the liquid to lower its temperature to freeze the liquid, or may change the freezing point of the liquid. The open channel may be completely filled with liquid, or, for liquids which expand when frozen, may be partially filled with enough liquid such that, once the liquid is frozen, it forms the desired shape of the rest of the channel. The extent to which the open channel is filled with liquid may be chosen to take account of the liquid changing in volume when it is frozen. Further, when the liquid is disposed in the open channel, the surface tension of the liquid may form a meniscus, which may have a shape which is convex when viewed in cross-section. That is, the channel is filled such that its surface extends above the surface of the layer in which the channel is disposed. When the liquid is frozen, the change in volume may cause the frozen liquid to expand or shrink, thus providing the desired shape of the support material in the channel.

The liquid 15 in the open channel is then frozen (i.e. undergoes a phase change). The frozen liquid acts as a support material, which allows a second layer of polymer to be disposed on top of the first layer, and a closed channel formed between the first and second layers. In other words, the frozen liquid fills the space which will form the channel once the architecture has been formed. It will be understood that the terms "frozen" and "freezing" refer generally to solidifying a liquid. This term is not limited to the use of any particular temperature or liquid, and may be used to describe the process of changing the temperature of any liquid so that its phase changes to the solid phase.

The freezing may take place at any suitable temperature, but the temperature is preferably low enough such that the liquid remains frozen during at least part of the subsequent process of curing the second layer, such that the frozen liquid can support the uncured liquid layer in the region of the channels. In particular, the freezing may take place at −30 degrees Celsius or less, preferably −50 degrees Celsius or less, and more preferably −80 degrees Celsius or less.

The freezing may be carried out by placing the first layer and the liquid in the channel in an atmosphere of the appropriate temperature. Alternatively, or additionally, local cooling may be applied to the liquid in the channel to bring it to the desired temperature.

Figure 5:
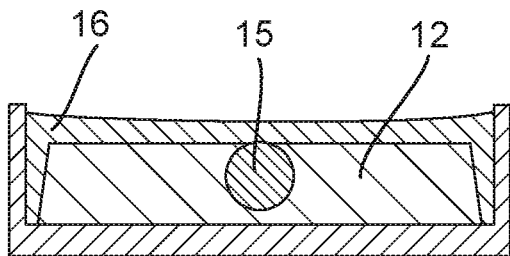
FIG. 5 shows the arrangement of FIG. 4 with the addition of a second layer of uncured polymeric material after the liquid has been solidified.

After the step of freezing the liquid, as shown in FIG. 5, an uncured polymeric material is poured onto the first layer 12 to form a second layer 16. Thus, the frozen liquid is encapsulated between the first layer and the second layer, and a closed channel is formed around the frozen liquid 15, defined between the first and the second layers 12, 16. In other words, the frozen liquid 15 supports the part of the second layer 16 which is over the open part of the channel, and this part of the second layer closes the channel. The second layer 16 may be poured into a second mould 14, in which the first layer 12 is disposed before pouring of the second layer 16.

Figure 6:
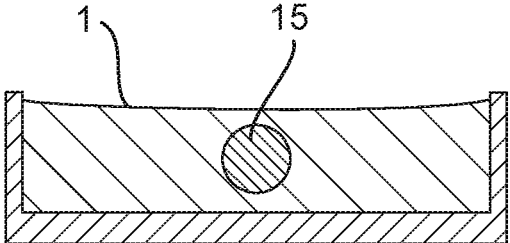
FIG. 6 shows the arrangement of FIG. 5 after curing of the second layer.
Figure 7:
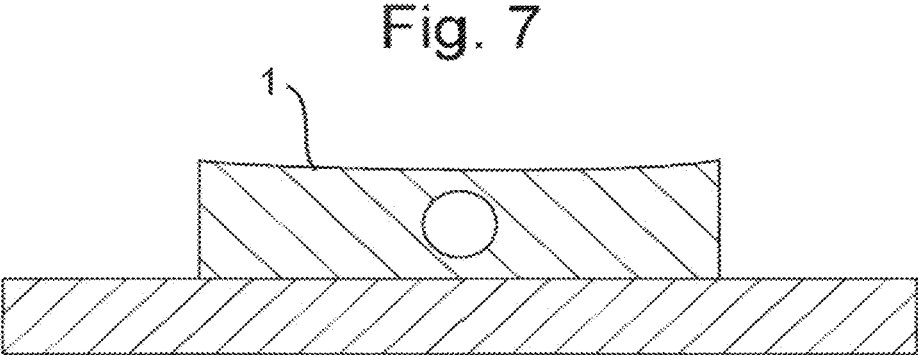
FIG. 7 shows the microfluidic architecture after removal of the liquid.

The second layer 16 is then at least partially cured. During the curing process of the second layer, crosslinks (i.e. chemical bonds) may develop between the first layer 12 and the second layer 16 to join the first and second layers. This may result in the architecture forming one continuous block 1, as shown in FIGS. 6 and 7. In other words, once the curing of the architecture has been completed, the first and second layers may no longer be separately identifiable, particularly if the first and second layers are formed using the same material. It will be appreciated that, if the first and second layers have different mechanical properties or are formed of different materials to each other, the layers are still joined but may nonetheless be separately identifiable.

After the second layer is cured, or during the process of curing the second layer, the frozen liquid (i.e. the support material) undergoes another phase change. The frozen liquid may be allowed to return to a liquid state (i.e. to melt), and is removed from the channel. Alternatively, the solid may change phase directly to a gas (i.e. sublimate). The support material may be removed using air, either by suction, by blowing air through the channel, or by any other suitable process. The finished architecture 1, with the liquid removed, is shown in FIG. 7.

The method as described above allows channels of very small diameter to be formed in the microfluidic architecture. Further, because the substance which supports the channel (i.e. the support material) when the second layer of uncured polymer is poured is a liquid, it can easily be removed once it has melted.

In the arrangement described above, a liquid 15 is used as the support material, and thus the liquid is solidified by freezing it. However, the support material may initially be a gas, and the phase transition may be from a gas to a liquid, then to a solid, or may be directly from a gas to a solid.

In another arrangement, the support material may be a solid, rather than a liquid or a gas, when it is disposed on the first layer. For example, a pattern may be formed using the support material, with the shape of the pattern corresponding to the shape of the channels which are to be formed. A first layer of polymeric material is formed by pouring the uncured polymeric material into a mould, and the first layer is at least partially cured. In contrast to the arrangement described above, (open) channels need not be formed in the first layer by the mould during formation of the first layer.

After the first layer is at least partially cured, the pattern is placed on the first layer, and the uncured elastomer is poured on top of the first layer and the pattern to encapsulate the support material, forming the second layer. The second layer is then at least partially cured. The support material may then undergo a phase change after the second layer has been formed and/or during the curing process of the second layer. In some arrangements, the solid may change to a liquid phase (i.e. melt, as described above). In other arrangements, the solid may sublimate (i.e. change directly to a gas phase from the solid phase). In both cases, the support material may be removed once it has undergone the phase change. The phase change may be caused by exposing the architecture to a change in temperature or pressure, or may occur at ambient temperature. Suitable materials which can be used for a support material which can sublimate include, but are not limited to, naphthalene and dry ice (solid carbon dioxide).

The above arrangement, in which the support material is a solid when disposed on the first layer, also allows channels of very small diameter to be formed in the microfluidic architecture. Further, because the substance which supports the channel (i.e. the support material) undergoes a phase change, it can easily be removed after the phase change. It will be understood that such a phase change may provide for easier removal of the support material than known arrangements in which, for example, a material is dissolved.

Figure 14:
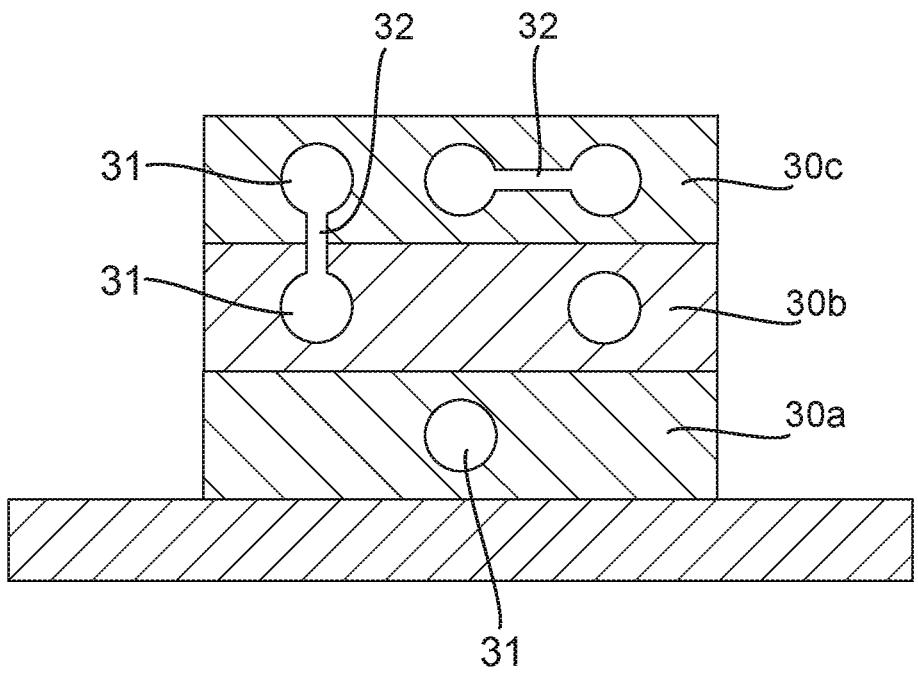
FIG. 14 shows a microfluidic architecture with three layers, and interconnections between layers.

Both of the methods described above may be extended to include forming further layers on the architecture. This may allow layers to be "stacked" on top of each other, with multiple channels or networks of channels disposed in the same architecture. The channels in different layers may also be interconnected by openings between those layers, allowing fluid communication between channels in different layers. Such a configuration is shown in FIG. 14, and described below.

In order to form such an architecture, an uncured polymeric material may be poured into a mould to produce a third layer comprising at least one open channel. It will be understood that the mould may be of the same shape as the mould used in forming the first layer, or may be of a different shape, depending on the desired shape of the channels in the third layer. The mould may include one or more raised parts in the mould which extend above the level to which the uncured polymer is poured, in order to provide openings as described below. These may allow interconnections between the third layer and the other layers.

The third layer is then at least partially cured so that it retains the shape defined by the mould. As with the first layer, if the third layer is partially cured, the layer may maintain the shape defined by the mould once it is removed from the mould, but may still retain the capacity to form further bonds with (i.e. to join to) further layers of polymeric material.

Once formed, the third layer is disposed on the second layer, with the surface of the third layer which does not have the open channel in contact with the second layer. This may be done whilst the second layer is partially cured. This allows the second and third layers to be subsequently cured together, such that bonds are formed between the second and third layer. That is, the third layer is joined to the second layer.

After the third layer has been joined to the second layer, the steps of closing the open channel in the third layer, as described above in relation to the first and second layer, are carried out. That is, the open channel in the third layer is at least partially filled with a liquid (which is an example of a fluid), and the liquid in the open channel is then frozen (i.e. solidified).

After the step of freezing the liquid, an uncured polymeric material is poured onto the third layer to form a fourth layer. Thus, the frozen liquid is encapsulated between the third layer and the fourth layer, and a closed channel is formed around the frozen liquid, defined between the third and the fourth layers. In other words, the frozen liquid supports the part of the fourth layer which is over the open part of the channel. Thus, a closed channel is formed.

The fourth layer is then at least partially cured. During the curing process of the fourth layer, cross-links (i.e. chemical bonds) may develop between the third layer and the fourth layer, such that the architecture forms one continuous block. In other words, once the architecture has been completed, the third and fourth layers are joined to each other. During this step, further cross-links may also be formed between the second and third layers. In some arrangements, the third and fourth layers may no longer be separately identifiable. It will be appreciated that, if the third and fourth layers have different mechanical properties or are formed of different materials to each other, the layers are joined but may nonetheless still be separately identifiable.

After the fourth layer is cured, or during the process of curing the fourth layer, the frozen liquid returns to a liquid state, and is removed from the channel. The liquid may be removed using air, either by suction or blowing air thorough the channel, or by any other suitable process.

When third and fourth layers are added to the architecture as described above, the steps of curing of the various layers may be timed so as to provide cross-linking between each of the layers that are in contact with each other. That is, all of the layers may be partially cured when they are first formed, and each subsequent layer may be disposed on the previous layer before curing of the previous layer is complete. This may ensure the structural integrity of the block, and allow the properties of the block to be controlled during manufacture by controlling the curing of each layer.

It will be understood that the steps above can be carried out as many times as required to dispose additional sets of channels in the architecture, stacked in further layers. In other words, the steps of adding additional layers, as described above in relation to the third and fourth layers, can be repeated multiple times in order to create a multi-layered architecture. It will also be understood that the arrangement using an initially solid support material may be used for some layers, and that the arrangement using an initially liquid support material may be used for other layers in the same architecture.

A schematic representation of such a multi-layered architecture, comprising three architecture layers, is shown in FIG. 14, which shows a view similar to that of FIG. 7, but with multiple channels 31, and interconnections 32 between some channels in the same layer and between layers 30a, 30b, 30c. It will be understood that each of the architecture layers 30a, 30b, 30c in the finished architecture may be produced by the process above, such that each layer is made by combining two individual layers of polymeric material. That is, the first layer and second layer described above make up the first architecture layer 30a, and the third layer and fourth layer described above make up the second architecture layer 30b. Although joins between the layers 30a, 30b, 30c are shown in FIG. 14, it will be understood that these joins may not be separately identifiable in the finished architecture. The interconnections 32 may be formed using the same process as the channels 31 themselves. Thus, the interconnections may also be considered as further channels disposed within the architecture.

The arrangement in FIG. 14 contains three architecture layers 30a, 30b, 30c, with an interconnection between a channel in the first layer and a channel in the second layer, and with an interconnection between two channels in the third layer. However, it will be understood that this is merely an exemplary arrangement, and that any other combination of interconnections between channels in the same architecture layer and in different architecture layers is possible.

In addition to the above methods including a support material which undergoes a phase change, in some arrangements, an additional support material may be used which does not undergo a phase change. In one arrangement, the additional support material may remain inside the finished architecture. In such an arrangement, the additional support material may be a substantially flat, flexible sheet. Such a sheet may be a sheet of of waxed paper, waxed plastic or a sheet of paper or plastics material coated with another organic coating, a metal foil (such as aluminium foil), or a sheet formed of or comprising an organic polymer. The thickness of such a flat, flexible sheet may be less than 1 mm, and preferably 0.3-0.7 mm, more preferably substantially 0.5 mm.

The use of an additional support material which does not undergo a phase change may be of particular use in forming architectures where channels extend in different directions within a given architecture layer. In some arrangements, it may be desired for such channels to cross each other without being in fluid communication with each other. This may be difficult to achieve in arrangements where the support material is initially fluid during the formation of the channels, because channels within the same architecture layer are filled with a single continuous stretch of fluid, which results in the finished channels being merged (i.e. in fluid communication) with each other. Further, it may be desired to provide channels which bridge two of the individual layers 12, 16 which are formed during the process of making a single architecture layer, or bridge between finished architecture layers.

In order to provide separation of channels in the same architecture layer which cross each other, or which bridge layers as described above, an additional support material as described above may be used. A process using such an additional support material is shown in FIGS. 15-20 and described below.

The additional support material is disposed on the first layer 12 during the process, in addition to the (main) support material 15. When a flat sheet is used, this may provide a "break" in the polymer, formed during the pouring of the polymer, which forms a discontinuity in the polymer of the finished architecture. This discontinuity may in turn form an additional channel.

In the process shown in FIGS. 15-20, FIG. 15 shows a first layer 12, similar to that shown in FIG. 3, but with three channels 13a, 13b, 13c. It will be understood that in the finished architecture, the channels 13 extend in a direction "into the page" in the cross section shown in FIG. 15.

Figure 20:
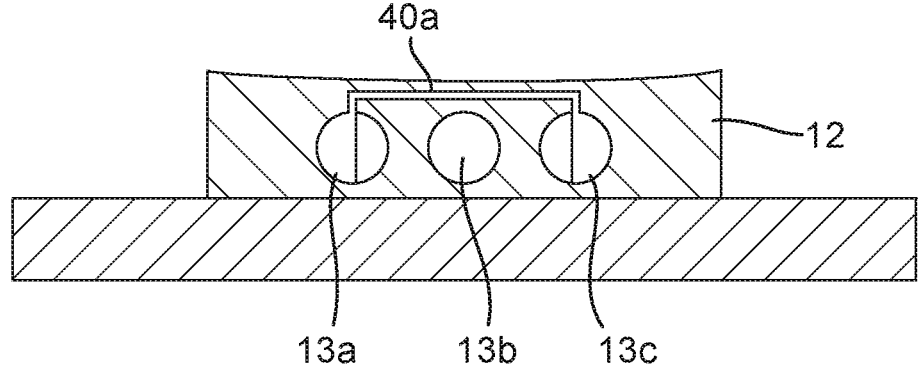
FIG. 20 shows the architecture of FIG. 19, with the additional channel visible and the support material retained in the architecture.

The use of an additional support material 40 allows an additional channel 40a to be formed (as shown in FIG. 20), spanning between the outer two channels 13a and 13c, and bypassing the middle channel 13b. The additional channel 40a extends in a direction from left to right in the view of FIG. 20. That is, the additional channel 40a extends in a direction perpendicular to the channels 13. In other words, the additional channel 40a crosses channel 13b without being in fluid communication with it, as described above, and links or bridges between channels 13a and 13c.

Figure 15:
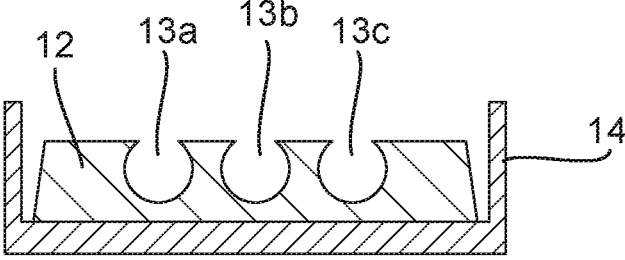
FIG. 15 shows a cured first layer including three open channels.
Figure 16:
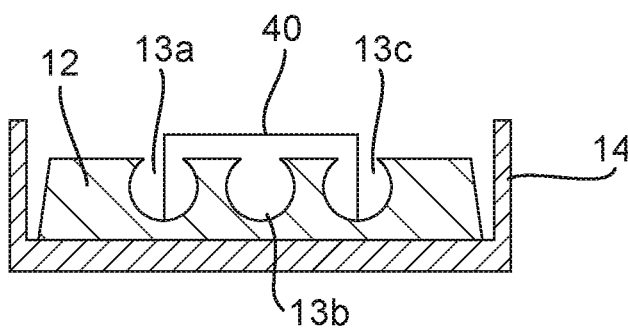
FIG. 16 shows the arrangement of FIG. 15, with an additional support material.

After the first layer 12 shown in FIG. 15 has been formed (by the same process as described above in relation to FIG. 3), an additional support material 40 is provided, on the first layer 12, inside the channels 13, and in the desired shape of the additional channel 40a. It will be understood that the additional support material need not extend along the entire length of the channels 13, but extend only partially along the length of the channel in a direction "into the page".

Figure 17:
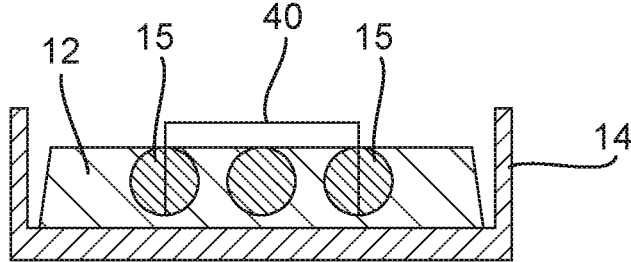
FIG. 17 shows the arrangement of FIG. 16, with the open channels filled with a liquid.

Once the additional support material 40 has been provided, the support material 15 (which can be considered as a "main" support material in this arrangement) is provided, as in the processes described above. For example, a liquid may be poured into the channels 13, and the liquid support material frozen, as described above in relation to FIG. 4. FIG. 17 shows a view of FIG. 16 after the support material 15 has been added, with the additional support material 40 being disposed within the (main) support material 15 and thus within the channels 13.

Figure 18:
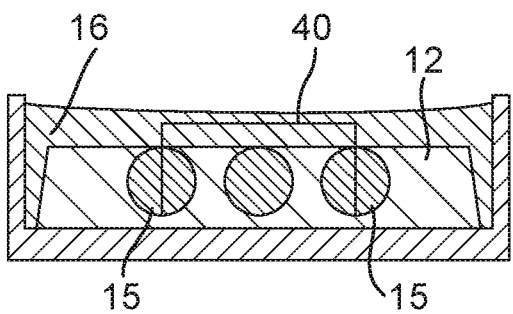
FIG. 18 shows the arrangement of FIG. 17 with the addition of a second layer of uncured polymeric material after the liquid has been solidified

FIG. 18 shows the arrangement of FIG. 17 after the second layer 16 has been provided, analogously to the second layer added in FIG. 5 to the arrangement of FIG. 4. The presence of the additional support material 40 in the first and second layers creates the discontinuity described above.

Figure 19:
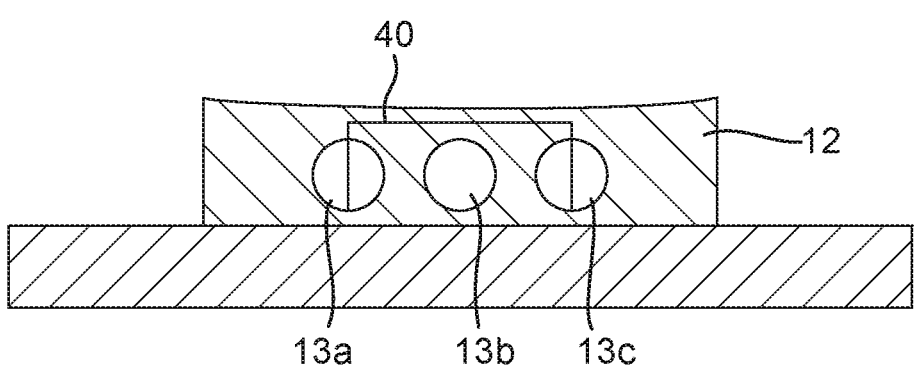
FIG. 19 shows the architecture formed in FIGS. 15-18 after removal of the liquid.

FIG. 19 shows the finished architecture, with three channels 13a, 13b, 13c and the additional support material 40 retained in the finished architecture. The additional channel 40a, as shown in FIG. 20, may either naturally form around the additional support material 40, or may open up around the discontinuity caused by the additional support material when a fluid is provided in the architecture.

In one arrangement, the additional support material is shaped such that one channel is displaced relative to each other in a direction perpendicular to the direction in which the channel extends (i.e. in the vertical direction in the view of FIG. 7). Because the additional support material is a substantially flat flexible sheet, it may abut the wall of the channel once the closed channel is formed, and does not interfere with the channel, or it may stay disposed within the channel without blocking flow through the channel, because of its thickness. Thus, it does not need to be removed from the architecture, and is retained in the finished architecture. The support material which does undergo a phase change (i.e. the main support material) can be removed, as described above, with the additional support material remaining in place.

Further, the additional support material may have the further function of interacting with the fluid in the channel in an advantageous manner. The interaction may be a chemical interaction or a physical interaction. For example, the additional support material may have a substance embedded therein, which can be absorbed from the additional support material by a fluid in the channel. This may allow the properties of the fluid to be modified. In another example, the additional support material may act as a filter to remove substances from a fluid in the channel (i.e. to absorb substances from the fluid, rather than the fluid absorbing substances from the additional support material). In another example, the additional support material may contain a substance which is retained in the additional support material, but causes a chemical reaction in the fluid in the architecture. Thus, the additional support material may have two functions, namely its function in forming the channel, as described above, and in interacting with the fluid in the finished architecture.

It will also be understood that, in some arrangements, a support material which does not undergo a phase change during the process of forming the channel may be used, without the use of a support material which does undergo a phase change during the process of forming the channel. Such a support material may be, for example, the substantially flat, flexible sheet (as described above as an "additional support material"). It will be understood that in such arrangements, the flexible sheet acts as a (main) support material, rather than an additional support material. In other words, the support material which does not undergo a phase change during the process of forming the at least one channel, and is retained between the first and second layers, replaces the support material which undergoes a phase change.

The polymeric material used in the method above may be any curable polymer. In particular, the polymer elastomeric material (i.e. an elastomer) or a thermosetting material. The elastomeric material may be (but is not limited to) one or more of a silicone, PDMS (polydimethylsiloxaneacrylic), a nitrile, a rubber, and polyurethane. The materials used for the first and second layers may be the same or different, and any combination of the after mentioned materials may be used. The polymeric material may be chosen according to the desired properties of the microfluidic architecture. For example, if a flexible architecture is desired, silicone may be particularly suitable, or if a more rigid architecture is desired, more rigid polymers (such as acrylic) may be used. Different materials may be used for different layers, which may be used to combine properties of different materials (for example, to produce a semi-rigid architecture in which one layer, and thus one part of the architecture, has a different rigidity to another layer).

Figure 8:
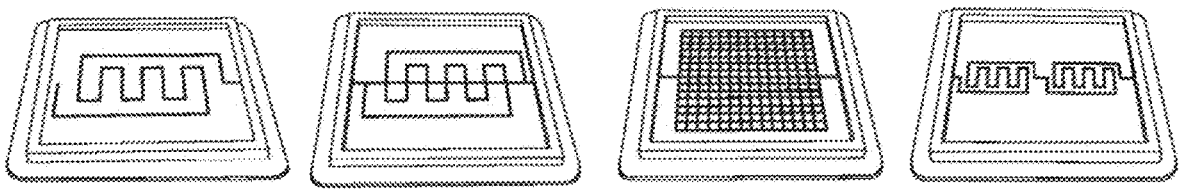
FIG. 8 shows a variety of moulds for use in a method of manufacturing a microfluidic architecture.
Figure 9:
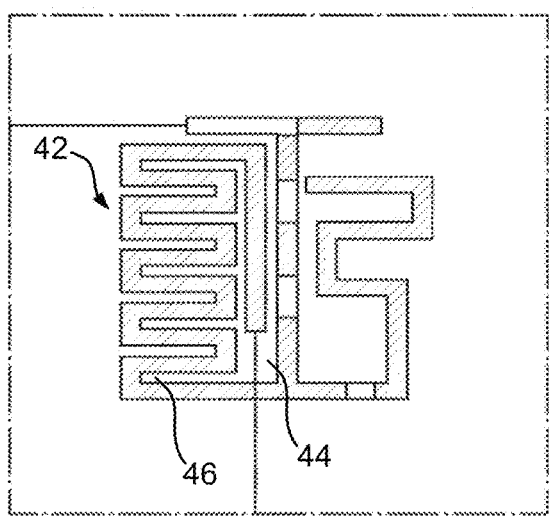
FIG. 9 shows an example of a network of channels in a microfluidic architecture.

The moulds which are used in the above method may be manufactured using additive layer manufacturing (3-D printing), and moulds may be produced as part of the method to provide the required layout of channels. However, the moulds may also be produced by any other suitable process. Examples of suitable moulds are shown in FIG. 8.

The microfluidic architecture resulting from the above method may form a flexible sheet. In other words, the sheet may have two main surfaces separated in a thickness direction. The two main surfaces may extend substantially parallel to each other. The remaining surface or surfaces may extend in in the thickness direction (i.e. a direction perpendicular to the directions in which the main surfaces extend). These remaining surfaces may have a smaller area than the main faces, and can be considered to be side surfaces or edges of the sheet. In some arrangements, the sheet may have a square or rectangular shape, such that the architecture has a cuboidal shape, with two of the faces being much larger than the rest of the faces, with the rest of the (smaller) faces forming the edges in the thickness direction.

It will be understood that the flexible sheet is not limited to this particular shape, but rather that different geometries of flexible sheets are within the scope of the disclosure. The flexible sheet can be any shape suitable for acting as an interface between rigid surfaces, including parabolic, annular, planar, or a combination of some or all of these geometries.

In some arrangements, the architecture includes one or more openings into the channel. That is, the opening or openings allow fluid to be introduced into, or removed from, the architecture.

In some arrangements, there may be two openings on opposite sides of the architecture. These may be on the side surfaces in the thickness direction. This may allow fluid to be introduced into the architecture and flow through the channel(s). For example, the openings may be disposed on opposite edge surfaces of the sheet such that fluid can be introduced through one opening and removed through another opening.

As explained above, the at least one channel may be a network of channels. That is, there may be several distinct channels disposed in the architecture, which may be joined together or may be separate from each other. An example of such a network of channels is shown generally at 42 in FIG. 9. In some arrangements, the network of channels 42 may include a manifold 44 and several branches 46 in fluid connection with the manifold. The manifold 44 may be a channel which forms a space arranged to store and/or retain fluid therein. The branches 46 may be directly or indirectly (e.g. through a valve, not separately shown) connected to the manifold 44, such that fluid can be supplied to the branches from the manifold.

Figure 10:
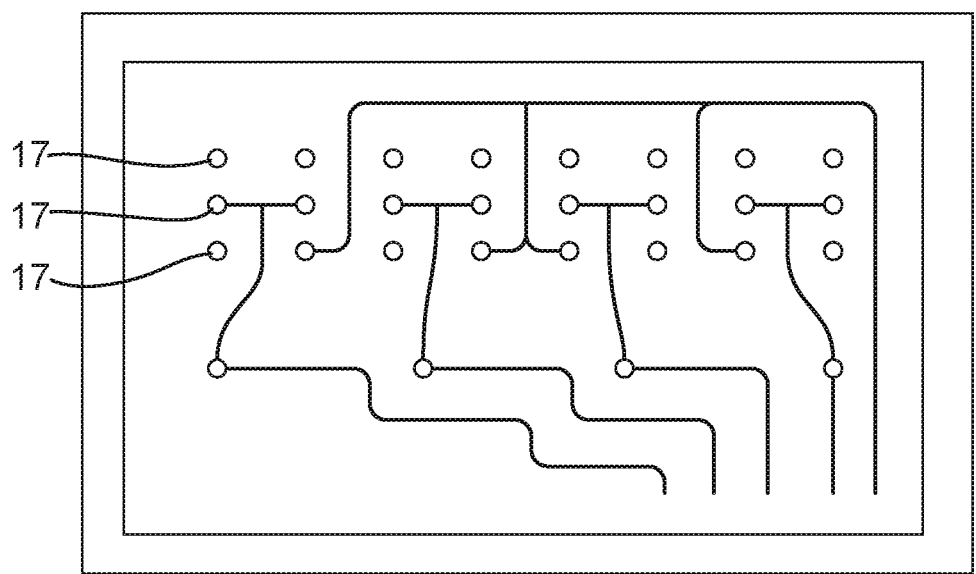
FIG. 10 shows an architecture including through-holes.

Additionally, one or more openings may be provided in a main surface of the architecture, as shown in FIG. 10. Such openings may be formed during the process of forming the first layer, by the provision of raised parts in the mould which extend above the level to which the uncured polymer is poured. These may take the form of posts (or columns) 18 which extend from the base of the mould. FIG. 11 shows a corresponding mould which can be used to produce such a layer. Thus, when the cured first layer is removed from the mould, a through-hole 17 is present in the first layer which subsequently forms an opening in the channel in the main surface of the architecture. The raised parts in a mould may also be used for other purposes. For example, when a layer with through holes into a channel has been formed, they may be used to block the holes while the channel is filled with liquid, to prevent the liquid from leaking out before it is frozen. Further, moulds used to form subsequent layers (e.g. the second mould 14 as described above) may include posts 18 which correspond to through-holes 17 in layers which have already been formed. These posts can be used to block the holes during the pouring of uncured polymer of subsequent layers, and to form further holes in the subsequent layer which are aligned with the holes in the layer which has already been formed.

Openings in the main surface of the architecture may serve a variety of purposes. For example, other components, such as electronic components or fluid control components may be mounted into the architecture (i.e. disposed through at least one of the openings). For example, valves may be inserted into the through holes (i.e. mounted to the architecture) in order to control the flow through the channel. Electronic components may also be mounted to the architecture via a tubing which is in fluid communication with an opening.

In some arrangements, there may be one or more channels (e.g. branches, as described above) which are not directly linked together (i.e. linked together inside the architecture). Rather, one or more valves may be provided which can be arranged such that the valves selectively allow or prevent fluid communication between two channels. In some arrangements, the valves may be electronic or pneumatic valves which are mounted to (or in) the architecture. This may allow the architecture to be used as a flow control component.

Further, in some arrangements, a channel of the architecture may itself act as a valve to allow or prevent flow through another channel of the architecture. That is, one channel may be arranged such that, when it is filled with fluid, its volume changes so that it blocks another channel. Again, this may allow the architecture to be used as a flow control component, and to control the flow of fluid through the architecture itself.

The microfluidic architecture may be used in a liner for a device such as a prosthetic, or other device which is in contact with a body part. For example, the objects or surfaces may be medical or non-medical devices which are arranged for skin contact. The liner may also include a number of chambers which are arranged to store or retain a fluid. In some arrangements, the channel is arranged to receive a fluid to cause an increase in at least one of the surface area or the volume of the microfluidic architecture, which may provide for improved cushioning of the body part, or gripping of the body part. An example of this is explained below with reference to FIGS. 12 and 13.

Figures 12, 13:
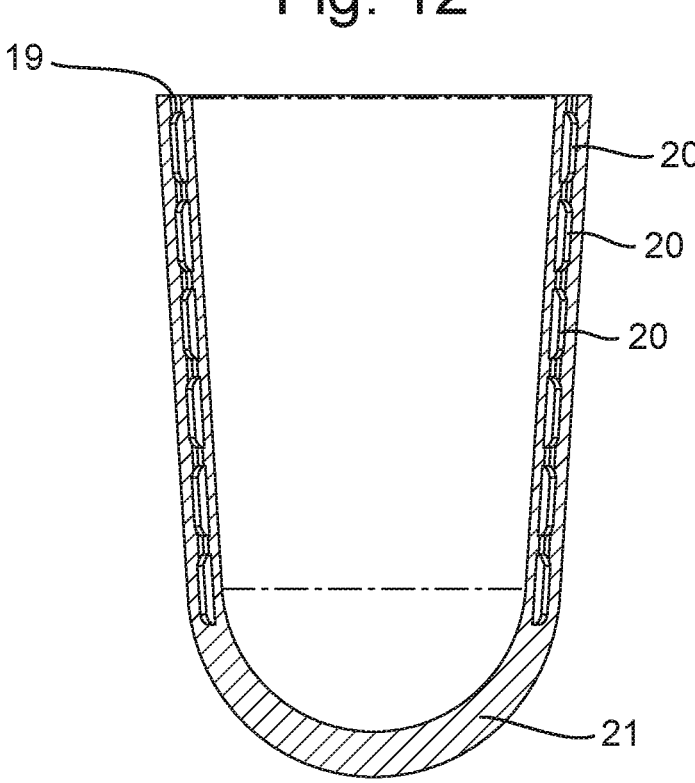
FIG. 12 shows a liner in a prosthetic.
FIG. 13 shows a liner in a prosthetic with fluid supplied to its chambers.

FIGS. 12 and 13 show an example of a liner 19 having a plurality of chambers 20 implemented in a prosthetic 21. The chambers 20 are connected by channels (and indeed the chambers and channels can together be considered a network of channels as described above. That is, the chambers themselves are also channels. FIG. 12 shows a state in which the chambers 20 are not filled with a fluid, and thus have a small volume. FIG. 13 shows a state in which fluid is supplied to the chambers 20. The fluid may be supplied via one or more openings as described above, and any number of chambers can be supplied through any number of openings.

When a fluid is supplied to an opening, the chambers 20 may be partially or entirely filled with the fluid. If the fluid is a gas, the fluid may fill an entire volume of the chambers 20. When the fluid is supplied, the chambers may increase in volume. The increase in volume of the chambers may cause an increase in surface area and/or volume of the liner (i.e. of the architecture) at the localised region of the liner corresponding to a respective chamber. This increase in volume may be at an interior surface of the liner 10 and/or at an exterior surface of the liner. In some examples, the chambers 20, when filled with fluid, may extend beyond the thickness of the unfilled liner (i.e. of the unfilled architecture). The increase in volume and/or surface area is caused by increased pressure within the chambers caused by the supply of fluid. Hence, it is apparent that the increase in surface area and/or volume of the liner at a localised region of the chambers is controllable by varying the fluid supplied to the chamber.

Further, the architecture is not limited to use as a liner between a body part and a prosthetic, but rather is suitable for acting as an interface between any suitable objects. In some non-limiting examples, the architecture can be used to provide cushioning in a ski boot, on a wheelchair, on a mattress, or in a helmet.

It should be understood by those skilled in the art that while the present invention has been described with reference to exemplary embodiments, it is not limited to the disclosed exemplary embodiments. Various modifications, combinations, sub-combinations and alterations may occur depending on design requirements and other factors insofar as they are within the scope of the appended claims or the equivalents thereof. Features from any example or embodiment of the present disclosure can be combined with features from any other example or embodiment of the present disclosure.

The invention claimed is:

1. A method of manufacturing a device having a fluidic architecture comprising at least one channel disposed therein, the method comprising:
    pouring a first polymeric material in an uncured state into a mould to produce a first layer;
    at least partially curing the first layer;
    disposing a support material on the first layer, the support material comprising a substantially flat sheet of material;
    pouring a second polymeric material in an uncured state to be in contact with the first layer and the support material to form a second layer to thereby encapsulate the support material; and
    curing the second layer such that bonds are formed between the first layer and the second layer to provide a block having an internal discontinuity immediately adjacent the support material, the discontinuity having an interior sidewall formed by at least a portion of the second layer which normally conforms to the support material and which is displaced away from the support material to form a channel responsive to introduction of a fluid within the block and along the support material, wherein the support material does not undergo a phase change.

2. The method of claim 1, wherein each of the first polymeric material and the second polymeric material is an elastomeric material comprising one or more of a silicone, acrylic, a nitrile, a rubber, and polyurethane.

3. The method of claim 1, further comprising:
    pouring a third polymeric material in an uncured state into a mould to produce a third layer;
    at least partially curing the third layer;
    disposing the third layer on the second layer before the curing of the second layer is complete; and
    curing the second and third layers together such that bonds are formed between the second layer and the third layer.

4. The method of claim 1, wherein the first polymeric material and the second polymeric material are the same material.

5. The method of claim 1, wherein the first polymeric material and the second polymeric material are different materials.

6. The method of claim 1, further comprising disposing an electronic component within the block.

7. The method of claim 1, wherein the channel forms a portion of a network of channels.

8. The method of claim 7, wherein the network of channels includes a manifold arranged to receive and/or store a fluid and a plurality of branches in fluid connection with the manifold.

9. The method of claim 1, wherein the support material comprises waxed paper or a metal foil.

10. The method of claim 1, wherein the support material is further arranged to interact with the fluid disposed in the channel by absorbing a substance from the fluid or releasing a substance into the fluid.

11. The method of claim 1, wherein the device is a fluidic chip.

12. The method of claim 1, wherein the block comprises two channels joined in selective fluid communication by an electronic component.

13. The method of claim 1, wherein at least one of the surface area or the volume of the block increases responsive to the fluid passing through the channel.

14. The method of claim 1, wherein the block is incorporated into a liner for a device arranged for skin contact.

15. A method of manufacturing a device having a fluidic architecture comprising at least one channel disposed therein, the method comprising:
  pouring a first polymeric material in an uncured state into a mould to produce a first layer;
  at least partially curing the first layer;
  disposing a support material on the first layer, the support material comprising a substantially flat sheet of material;
  pouring a second polymeric material in an uncured state to be in contact with the first layer and the support material to form a second layer; and
  curing the second layer to join the first layer and the second layer together to form a block, the block having an internal discontinuity immediately adjacent the support material comprising an interior sidewall formed by at least a portion of the second layer that is not joined to the first layer and is configured to expand to form a channel responsive to introduction of a fluid along the support material, wherein the support material does not undergo a phase change.

16. The method of claim 15, wherein each of the first polymeric material and the second polymeric material is an elastomeric material comprising one or more of a silicone, acrylic, a nitrile, a rubber, and polyurethane.

17. The method of claim 15, further comprising:
  pouring a third polymeric material in an uncured state into a mould to produce a third layer;
  at least partially curing the third layer;
  disposing the third layer on the second layer before the curing of the second layer is complete; and
  curing the second and third layers together such that bonds are formed between the second layer and the third layer.

18. The method of claim 15, wherein the first polymeric material and the second polymeric material are the same material.

19. The method of claim 15, wherein the first polymeric material and the second polymeric material are different materials.

20. The method of claim 15, further comprising disposing an electronic component through at least one opening in the channel.

21. The method of claim 15, wherein the channel forms a portion of a network of channels.

22. The method of claim 21, wherein the network of channels includes a manifold arranged to receive and/or store a fluid and a plurality of branches in fluid connection with the manifold.

23. The method of claim 15, wherein the support material comprises waxed paper or a metal foil.

24. The method of claim 15, wherein the support material is further arranged to interact with the fluid disposed in the channel by absorbing a substance from the fluid or releasing a substance into the fluid.

25. The method of claim 15, wherein the device is a fluidic chip.

26. The method of claim 15, wherein the block comprises two channels joined in selective fluid communication by an electronic component.

27. The method of claim 15, wherein at least one of the surface area or the volume of the block increases responsive to the fluid passing through the channel.

28. The method of claim 15, wherein the block is incorporated into a liner for a device arranged for skin contact.

* * * * *